(12) United States Patent
Di Girolamo et al.

(10) Patent No.: US 9,403,744 B2
(45) Date of Patent: Aug. 2, 2016

(54) PROCESS FOR THE PRODUCTION OF ALKYL ETHERS BY THE ETHERIFICATION OF ISOBUTENE

(75) Inventors: Marco Di Girolamo, San Donato Milanese Milan (IT); Massimo Conte, Peschiera Borromeo Milan (IT); Antonio Sgambati, Milan (IT); Alberto Cipelli, Busseto Parma (IT)

(73) Assignee: SAIPEM S.p.A., San Donato Milanese (IT)

( * ) Notice: Subject to any disclaimer, the term of this patent is extended or adjusted under 35 U.S.C. 154(b) by 354 days.

(21) Appl. No.: 12/373,730

(22) PCT Filed: Jul. 12, 2007

(86) PCT No.: PCT/EP2007/006307
§ 371 (c)(1),
(2), (4) Date: Feb. 12, 2009

(87) PCT Pub. No.: WO2008/009409
PCT Pub. Date: Jan. 24, 2008

(65) Prior Publication Data
US 2009/0253942 A1    Oct. 8, 2009

(30) Foreign Application Priority Data

Jul. 18, 2006 (IT) .............................. MI2006A1390

(51) Int. Cl.
*C07C 41/01* (2006.01)
*C07C 41/06* (2006.01)

(52) U.S. Cl.
CPC ...................................... *C07C 41/06* (2013.01)

(58) Field of Classification Search
CPC ....................................................... C07C 41/06
See application file for complete search history.

(56) References Cited

U.S. PATENT DOCUMENTS

| 3,979,461 | A | | 9/1976 | Ancillotti et al. |
| 4,302,298 | A | * | 11/1981 | Mikitenko et al. ............... 203/75 |
| 4,324,924 | A | * | 4/1982 | Torck et al. .................... 568/697 |
| 4,554,386 | A | | 11/1985 | Groeneveld et al. |
| 5,015,783 | A | * | 5/1991 | Vora et al. ...................... 568/697 |
| 5,237,109 | A | | 8/1993 | Patton et al. |
| 2006/0065574 | A1 | * | 3/2006 | Koskinen et al. ............... 208/49 |

FOREIGN PATENT DOCUMENTS

| EP | 0 123 338 | 10/1984 |
| EP | 0 537 636 | 4/1993 |

* cited by examiner

*Primary Examiner* — Rosalynd Keys
(74) *Attorney, Agent, or Firm* — Oblon, McClelland, Maier & Neustadt, L.L.P.

(57) ABSTRACT

Process for the production of alkyl ethers by the etherification of isobutene, contained in $C_4$-$C_5$ hydrocarbon streams, with linear alcohol, in the presence of acid catalysts, comprising the following essential steps: a) feeding the isobutene contained in $C_4$-$C_5$ hydrocarbon cuts, together with one or more streams containing linear alcohol, to a first reaction step; b) sending the stream leaving the first reaction step to a first distillation area, separating a light stream from a heavy stream containing the desired ether; c) feeding the light stream separated in the first distillation area, together with one or more streams containing linear alcohol, to a second reaction step; d) sending the stream leaving the second reaction step to a second distillation area separating a light stream from a heavy stream containing ether, $C_4$ hydrocarbons and alcohol which is recycled to the first distillation area; e) sending the light stream in the second distillation area to a recovery section of the linear alcohol contained therein; f) recycling the linear alcohol recovered in the recovery section to at least one of the two reaction steps. The present invention relates to plant solutions which allow the alcohol/isobutene molar ratio to be increased in the reaction steps and therefore maximizing the conversion of isobutene.

25 Claims, 8 Drawing Sheets

PROCESS FOR THE PRODUCTION OF ALKYL ETHERS BY THE ETHERIFICATION OF ISOBUTENE

This application is a 371 of PCT/EP07/06307 filed Jul. 12, 2007. Priority to Italian patent application MI2006A001390, filed Jul. 18, 2006, is claimed.

The present invention relates to a process for the production of alkyl ethers by the reaction, in the presence of acid catalysts, of a linear alcohol with isobutene, contained in $C_4$-$C_5$ hydrocarbon cuts, using innovative plant solutions which allow the alcohol/isobutene molar ratio to be increased in the reaction steps and therefore maximizing the conversion of isobutene.

For environmental reasons, the composition of gasolines is being reformulated in order to obtain fuels which burn better and have fewer evaporative emissions.

In order to be able to achieve this objective, it has been necessary to reduce the content of aromatic compounds, light olefins (photochemically reactive and precursors responsible for the formation of atmospheric ozone), sulfur, volatility (to minimize losses) and the final boiling point of the gasolines.

All of these measures have resulted in a contraction in the volume and an octane deficiency of the reformulated gasolines for which resort must be made to an increasing use of oxygenated compounds (alcohols and ethers) and purely hydrocarbon compounds such as alkylated products and iso-octane.

These latter compounds are capable of positively contributing to the above demands as they have a high octane number (both the Research Octane Number (RON) and the Motor Octane Number (MON) are high) excellent boiling point properties (limited volatility but low end-point) and they are practically free of olefins and aromatic compounds.

Alkylated products are currently obtained by reaction, in liquid phase, between isoparaffinic hydrocarbons, such as isobutane, and olefins, for example propylene, butenes, pentenes and relative mixtures, in the presence of an acid catalyst for the production of $C_7$-$C_9$ hydrocarbons with a high octane number to be used in gasolines (see for example C. Hodge, 2004 NPRA Am. Meet., San Antonio, Tex., paper AM-04-13 and the references contained therein).

Both of these traditional processes (with hydrofluoric acid and with sulfuric acid) are undergoing considerable difficulties which make their future uncertain, as a result of increasingly strict environmental regulations; the process using hydrofluoric acid due to the toxicity of this acid, especially in populated areas, and the process with sulfuric acid due to the large production of acid mud in addition to the extremely corrosive nature of the catalyst.

Alternative processes with solid acid catalysts are being developed, but their commercial applicability still has to be demonstrated.

Iso-octane, on the other hand, is obtained by hydrogenating the product of the selective dimerization of isobutene; this reaction is carried out in the presence of oxygenated compounds (U.S. Pat. No. 5,723,687, U.S. Pat. No. 6,011,191, U.S. Pat. No. 6,433,238, U.S. Pat. No. 6,500,999 and ITMI94/A001089) capable of moderating the activity of the catalyst and minimizing the formation of higher oligomers which have boiling points at the limit (trimers) or even higher (tetramers) than the specifications of gasolines. The main problem of the process for the production of iso-octane consists in the fact that it represents an alternative to etherification (both processes start from isobutene) but is clearly less convenient as, with a higher investment (mainly due to the hydrogenation section), there is a lower production as a result of the lack of contribution of alcohol.

The use of oxygenated products in gasolines, on the contrary, began in the Seventies' following the first energy crises (search for fuels or alternative components to petroleum) and the progressive elimination of lead-based additives. Oxygenated products initially had the double function of octane boosters and volume extenders obtained from alternative sources to petroleum; subsequently however it was discovered that oxygenated products also have the capacity of improving the combustion quality and consequently decreasing the discharge emissions of polluting compounds.

Alcohols (methanol and ethanol) were initially used as oxygenated compounds, which were subsequently substituted by ethers such as methyl ter-butyl ether (MTBE), ethyl ter-butyl ether (ETBE) and methyl ter-amyl ether (TAME).

Thanks to its higher properties, MTBE immediately appeared to be the oxygenated compound capable of dominating the market; MTBE does in fact combine high octane properties with a lower volatility with respect to alcohols, a complete miscibility with gasoline, no problem of phase separation in the storage and distribution system of gasoline, and finally it has the great advantage of being able to be easily synthesized starting from compounds not normally used in gasoline pools such as methanol and isobutene.

ETBE has very similar characteristics and in some cases better than MTBE (lower RVP and solubility in water), as shown in Table I, but it is jeopardized by the fact that the economical validity of its production depends on the benefit provided to ethanol.

TAME, on the other hand, cannot be considered as being a true "octane booster" as its production is effected to the detriment of the $C_5$ iso-olefins (2-methyl-1-butene and 2-methyl-2-butene) which are already characterized by the good octane properties.

The etherification of the $C_5$ cut however allows the general characteristics of the fraction to be improved as oxygen is introduced into the mixture and the olefin content and volatility of the mixture are reduced.

TABLE I

| properties of alkyl ethers | | | |
|---|---|---|---|
| | MTBE | ETBE | TAME |
| Oxygen, w % | 18.2 | 15.3 | 15.3 |
| Boiling point, ° C. | 55 | 73 | 86 |
| Density, g/cm$^3$ | 0.74 | 0.77 | 0.77 |
| Solubility in H$_2$O, w % | 4.3 | 1.2 | 1.1 |
| RON, blending | 118 | 118 | 111 |
| MON, blending | 101 | 102 | 98 |
| RVP, blending | 8 | 4 | 1 |

Etherification is an exothermic equilibrium reaction between a primary alcohol and an iso-olefin (with a double bond on a tertiary carbon atom) which takes place in the presence of an acidic catalyst, in gaseous or liquid phase, in relation to the operating pressure. This reaction is industrially carried out in liquid phase, at pressures of 1-2 MPa and relatively low temperatures (40-70° C.) so as to favour the thermodynamic conversion.

Methanol and ethanol are normally used as primary alcohols, which react with isobutene to form MTBE and ETBE, respectively. The alcohol/isobutene molar ratio to be used should be as high as possible, in order to direct the thermodynamic equilibrium towards the formation of ether; in the industrial plants for the synthesis of MTBE and ETBE there are in fact operative constraints, due to the maximum content of alcohol in the product and at the head of the separation columns, which oblige the use of molar ratios slightly higher than the stoichiometric value.

Even if numerous sources are available for providing hydrocarbon streams containing isobutene, isobutane, n-butane, n-butenes and $C_5$ hydrocarbons, the most common are those deriving from iso-paraffin dehydrogenation processes, FCC units, Steam Cracking units and from the dehydration of tert-butanol (from the synthesis of propylene oxide) or iso-butanol from conversions of $CO/H_2$ blends into methanol and higher alcohols (mainly iso-butanol).

If the Steam Cracking streams contain diolefins in addition to the desired mono-olefins, it is convenient to remove them by means of typical removal treatment (for example, extractions or selective hydrogenations). Table II shows the standard compositions of typical $C_4$ hydrocarbon fractions coming from different sources.

TABLE II

Typical compositions of $C_4$ streams (weight %)

| Product | Steam Cracking | FCC | Dehydrogenation | Dehydration |
|---|---|---|---|---|
| Isobutene | 30-50 | 10-25 | 45-55 | >90 |
| n-butenes | 35-60 | 25-50 | <1 | <10 |
| Butanes | 4-10 | 30-60 | 45-55 | <1 |

In the case of streams from dehydration, as a result of the high concentration of isobutene, it is suitable to dilute the feeding charge with $C_4$-$C_7$ hydrocarbons in order to have a better control of the reactor temperature.

In the case of refinery plants, (streams from FCC) a high conversion of isobutene (about 95%) is not required, as the etherification effluent is normally sent to an alkylation plant capable of converting all the olefins present in the stream; the typical configuration of the refinery plants is therefore the simplest possible and includes two reactors in series with an intermediate cooling area.

In the case of streams coming from Steam Cracking or the Dehydrogenation of isobutane, it is necessary to have conversions higher than 99% in order to minimize the isobutene content in the outgoing stream. For Steam Cracking plants, in fact, isobutene represents an impurity in the subsequent treatment of $C_4$ residues (metathesis and butene-1 polymerization), whereas in the case of streams from dehydrogenation, the stream at the outlet of the etherification plant (mainly consisting of isobutane) is recycled to the dehydrogenation reactor, where isobutene, when present, is transformed into coke with a consequent loss of raw material and reduction of the catalyst life.

The procedure now proposed is based on a more complex plant configuration, centered on a double reaction step, which allows an improvement in the conversion of the isobutene present in $C_4$-$C_5$ hydrocarbon streams.

Figure 1:
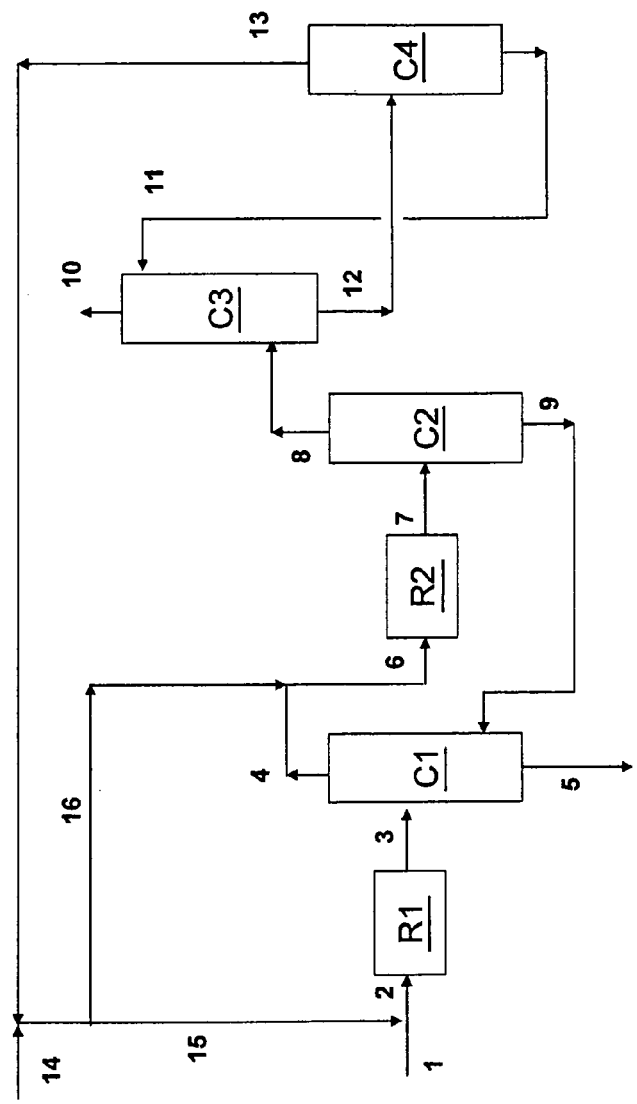
FIG. 1 shows a schematic diagram of a two-step etherification to prepare MTBE and ETBE according to an embodiment of the invention.

The procedure, object of the present invention, for the production of alkyl ethers by the etherification of isobutene, contained in $C_4$-$C_5$ hydrocarbon streams, with linear alcohols, in the presence of acid catalysts, comprises the following essential steps:

a) feeding the isobutene contained in $C_4$-$C_5$ hydrocarbon cuts, together with one or more streams containing linear alcohol, to a first reaction step;

b) sending the stream leaving the first reaction step to a first distillation area separating a light stream from a heavy stream containing the desired ether;

c) feeding the light stream separated in the first distillation area, together with one or more streams containing linear alcohol, to a second reaction step;

d) sending the stream leaving the second reaction step to a second distillation area separating a light stream from a heavy stream containing ether, $C_4$ hydrocarbons and alcohol which is recycled to the first distillation area;

e) sending the light stream in the second distillation area to a recovery section of the linear alcohol contained therein;

f) recycling the linear alcohol recovered in the recovery section to at least one of the two reaction steps.

In the $C_4$-$C_5$ hydrocarbon streams fed, diolefins can also be present whereas saturated and olefinic $C_5$ hydrocarbons may be present in various quantities (0.5-10%) depending on the efficiency of the $C_4$-$C_5$ separation step; the $C_5$ iso-olefins possibly present can be involved in the etherification reactions with the formation of TAME.

Furthermore, the isobutene content in the stream can be changed by dilution with $C_4$-$C_5$ hydrocarbon streams.

The linear alcohol is preferably selected from those having from 1 to 6 carbon atoms; more preferably from methanol and ethanol.

The linear alcohol, can react not only with isobutene, but also with $C_4$ and $C_5$ olefins present in the charge.

The recovery section of the linear alcohol can consist of a washing step with water or an adsorption step on inorganic solids.

If the washing step is selected, said step can be effected by feeding the light stream separated in the second distillation step, to a washing column with water, from whose head, a hydrocarbon stream is obtained having a low content of oxygenated products and from whose bottom a hydro-alcoholic stream is obtained which is sent to a distillation column from whose head the liner alcohol is recovered.

Various integrations can be effected on the general procedure claimed above, which further improve the results obtained, as specified hereunder.

The heavy stream containing the desired ether separated in the first distillation area, is preferably sent to a third distillation area, having one or more distillation columns, in which a stream consisting of substantially pure ether is separated from a stream containing the azeotropic alcohol/ether mixture and possibly other compounds (such as di-alkylether, $C_5$ hydrocarbons, tert-butyl alcohol, etc.), which is divided into two streams of which one is recycled to the first reaction step, the other joined to the stream consisting of substantially pure ether, so as to respect the alcohol content limits in the product.

The light stream leaving the first distillation area can be in condensed form (following a condenser, which can be situated downstream of the column or last distillation column) and can be partially recycled to the first reaction step.

The light stream leaving the second distillation area can be in condensed form (following a condenser, which can be situated downstream of the column or last distillation column) and can be partially recycled to the first and/or second reaction step.

The hydrocarbon stream with a low content of oxygenated compounds obtained at the head of the washing column can be optionally partially recycled to the first and/or second reaction step.

The light stream leaving the first distillation area in condensed form can be partially or totally sent to a washing section with water.

Two streams can leave said washing section with water, one containing water and linear alcohol preferably sent to the distillation column of the water washing step downstream of the second distillation area, the other, impoverished in oxygenated products, substantially containing $C_4$ hydrocarbons recycled, as reflux, to the first distillation area.

The light stream leaving the second distillation area in condensed form can be partially or totally sent to a washing section with water.

Two streams can leave said water washing section, one containing water and linear alcohol preferably sent to the distillation column of the water washing step downstream of the second distillation area, the other, impoverished in oxygenated products, substantially containing $C_4$ hydrocarbons recycled, as reflux, to the first distillation area.

The light stream leaving the first distillation area can be in gaseous form, without the use of a condenser, however, and in this case it can be sent to a quenching section.

Two streams leave said quenching section, downstream of the first distillation area, one containing water and linear alcohol which can be sent to the distillation column of the water washing step downstream of the second distillation area, the other, substantially containing $C_4$ hydrocarbons, which can be partially sent to the second reaction step and partially recycled, as reflux, to the first distillation area.

The light stream leaving the first distillation area can be in gaseous form, without the use of a condenser, however, and in this case it can be sent to another quenching section.

Two streams leave said quenching section, downstream of the second distillation area, one containing water and linear alcohol which can be sent to the distillation column of the water washing step downstream of the second distillation area, the other, substantially containing $C_4$ hydrocarbons, which can be partially sent to the washing column of the water washing step downstream of the second distillation area and partially recycled, as reflux, to the second distillation area.

In the second reaction step at least two reactors in series can be used, between which an intermediate cooling can be optionally present.

Part of the stream leaving the head of the distillation column of the water washing step or methanol can be fed to the second or last of the reactors in series of said second reaction step.

A wide variety of acid catalysts can be used for this process, among which, for example, mineral acids such as sulfuric acid, $BF_3$, supported phosphoric acid, suitably modified zeolites, heteropolyacids and sulfonated polymeric resins, for example Amberlyst 15, Amberlyst 35, Amberlyst 36, etc. can be mentioned. Among these catalysts, the use of macro-lattice sulfonated resins, generally copolymers of styrene and divinylbenzene, is preferred; the characteristics of these resins are widely described in literature (see for example A. Mitschker, R. Wagner, P. M. Lange, "Heterogeneous Catalysis and Fine Chemicals", M. Guisnet ed., Elsevier, Amsterdam (1988), 61).

A vast range of operating conditions can be used for producing alkyl ethers from isobutene by means of the object of the present invention. It is possible to operate in vapour phase or in liquid-vapour phase but the operating conditions in liquid phase are preferred.

The process, object of the present invention, can operate under either batch or continuous conditions, bearing in mind, however, that the latter are much more advantageous in industrial practice. The reactor configuration selected can be optionally selected from fixed bed reactors (tubular and/or adiabatic), stirred reactors and finally column reactors which also allow the separation of the products.

The range of process conditions, operating in liquid phase, includes a wide variety of operating conditions which are described hereunder.

The pressure is preferably superatmospheric to maintain the reagents in liquid phase, generally below 5 MPa, more preferably from 0.2 to 2.5 MPa. The reaction temperature preferably ranges from 30 to 100° C.

The feeding space velocities of the alcohol-hydrocarbon stream are preferably lower than $30\,h^{-1}$, more preferably from 1 to 15 $h^{-1}$.

The isobutene is mainly converted in the reaction area, part of the n-butenes however, even if in very low quantities, and $C_5$ iso-olefins can also be etherified.

To illustrate the present invention, FIG. 1 shows a typical two-step etherification scheme which can be used for the synthesis of MTBE and ETBE from dehydrogenation and Steam Cracking charges.

The hydrocarbon stream (1) containing isobutene, is sent together with the alcohol (15) to a first reaction step R1, which can consist of one or more reactors, in which the $C_4$ iso-olefin is selectively converted to ether.

The effluent (3) from the first reaction step is sent to a first separation column C1, where a stream (4) containing the azeotropic mixture alcohol/$C_4$ hydrocarbons is removed from the head, whereas a stream (5) containing the reaction product is removed from the bottom.

The stream at the head (4) is then fed, together with the alcohol reintegration stream (16), to a second reaction step R2, which can consist of one or more reactors, in which the etherification of isobutene is completed.

The effluent (7) from the second reaction step is sent to a column C2 from the bottom of which a stream (9) containing ether, part of the $C_4$ products and part of the alcohol, is removed and sent to the column C1 for the recovery of the product. The stream at the head (8), consisting of the azeotropic mixture $C_4$ compounds/alcohol, on the other hand, is fed to a washing column C3 with water (11) in order to obtain a hydrocarbon stream with a very low content of oxygenated products (10) which can be used in subsequent operations. The hydro-alcoholic stream (12) which leaves the bottom of the column C3, is sent to a distillation column C4 from whose bottom the water (11) is recovered, recycled to the column C3, and from whose head the alcohol (13) is recovered and can be added to fresh alcohol (14) and subsequently sent to the two reaction steps (streams 15 and 16). In the case of the synthesis of MTBE, pure methanol is recovered from the head of the $C_4$ column, whereas in the case of ETBE, the azeotropic mixture ethanol/water (93:7) is recovered. These two latter columns can alternatively be substituted by an absorption system with inorganic solids.

The limiting factor of this process scheme is the quantity of alcohol which can be fed to the two reaction steps and which determines the process yield; as the reaction is limited by the equilibrium, the greater the quantity of alcohol used, the higher the conversion will be of isobutene.

In practice, however, the quantity of alcohol which can be used is subject to the following restrictions:

there is a limit of the maximum content of linear alcohol (generally 2% by weight) in the ether produced;

the maximum quantity of alcohol which can be recovered from the head of the two fractionation columns C1 and C2 (streams 4 and 8) is limited by the composition of the alcohol/$C_4$ azeotropic mixture, indicated in Table III.

TABLE III azeotropic composition at atmospheric pressure

| | Boiling point, ° C. | A % | B % |
|---|---|---|---|
| Methanol/$C_4$ | −2 | 1.0 | 99.0 |
| Ethanol/$C_4$ | −1 | 0.2 | 99.8 |
| Methanol/MTBE | 51 | 14 | 86 |
| Ethanol/ETBE | 66 | 22 | 78 | the alcohol content in the streams at the head of the two columns must be kept within its azeotropic composition with the $C_4$ products to prevent the ether/alcohol azeotropic mixture (Table III) from also being removed from the head. The presence of ether in these streams must be avoided as, in the case of stream 4, it does not favour thermodynamic equilibrium in the second reaction step, whereas in the case of the hydrocarbon stream leaving the plant (8), the ether represents a poison, which cannot be eliminated like alcohol by washing with water, for the subsequent treatment of the stream (metathesis, polymerization).

Consequently, the maximum quantity of alcohol which can be fed to the plant is provided by the sum of the following contributions:

Alcohol=Converted alcohol+Alcohol in the ether+
Alcohol in the $C_4$ azeotropic mixture.

In spite of these restrictions, in the case of methanol, the thermodynamic equilibrium is favoured to such an extent as to allow, with a two-step configuration, the high conversions of isobutene requested (>99%) to be reached for feeds from Steam Cracking and Dehydrogenation. In the case of ethanol, on the contrary, the less favourable equilibrium and azeotropic mixture less rich in oxygenated products jeopardize the conversion and it is not possible to respect the specifications required for the outgoing $C_4$ products.

In this case, it is therefore necessary to increase the concentration of alcohol in the reaction steps by the use of innovative plant solutions capable of overcoming the restrictions indicated above.

Figure 2:
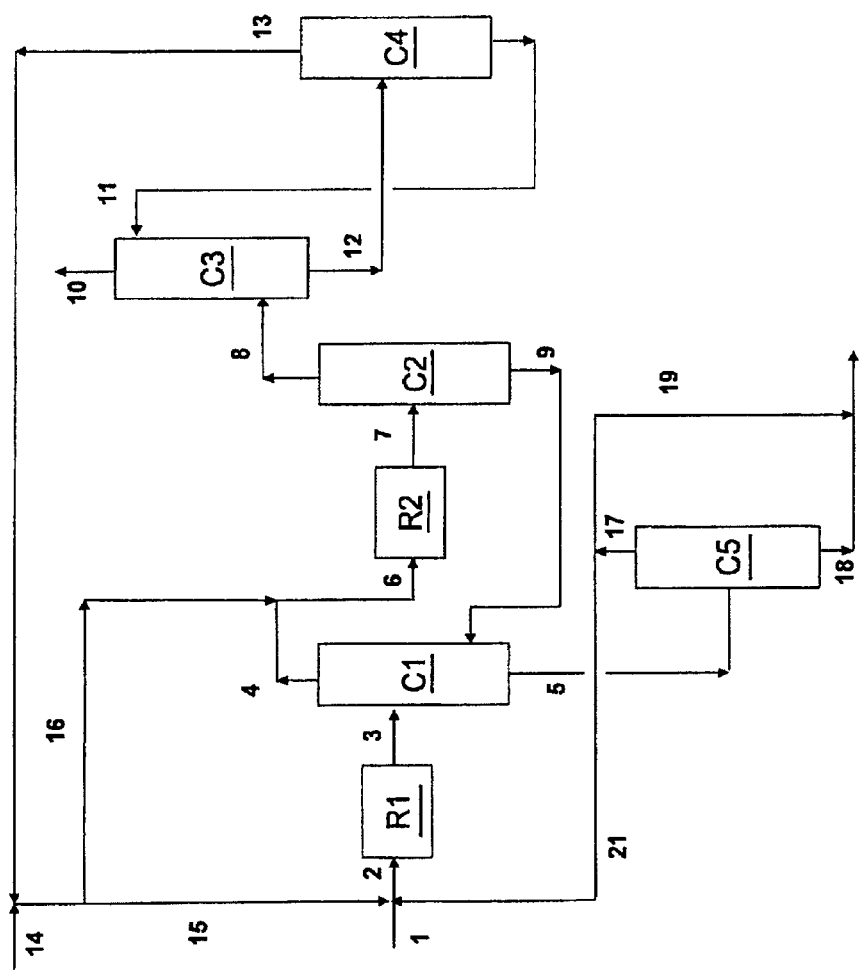
FIG. 2 shows a schematic diagram of an alternative embodiment of the invention wherein excess alcohol is recovered.

FIG. 2 shows a possible alternative scheme which envisages the recovery at the bottom of the column C1 of the excess alcohol used in the reaction together with the ether produced. In this case the ether/alcohol mixture (5) is then sent to a new distillation column C5 from whose bottom pure ether is recovered whereas a stream containing the ether/alcohol azeotropic mixture is recovered, which is subsequently divided so that a part (19) is joined with the ether (in such a quantity as to respect the specifications on the alcohol content in the product) whereas the remaining part (21) is recycled to the first reaction step where the presence of ether (thanks to the high content of isobutene in the initial feed) has a limited impact on the conversion.

Figure 3:
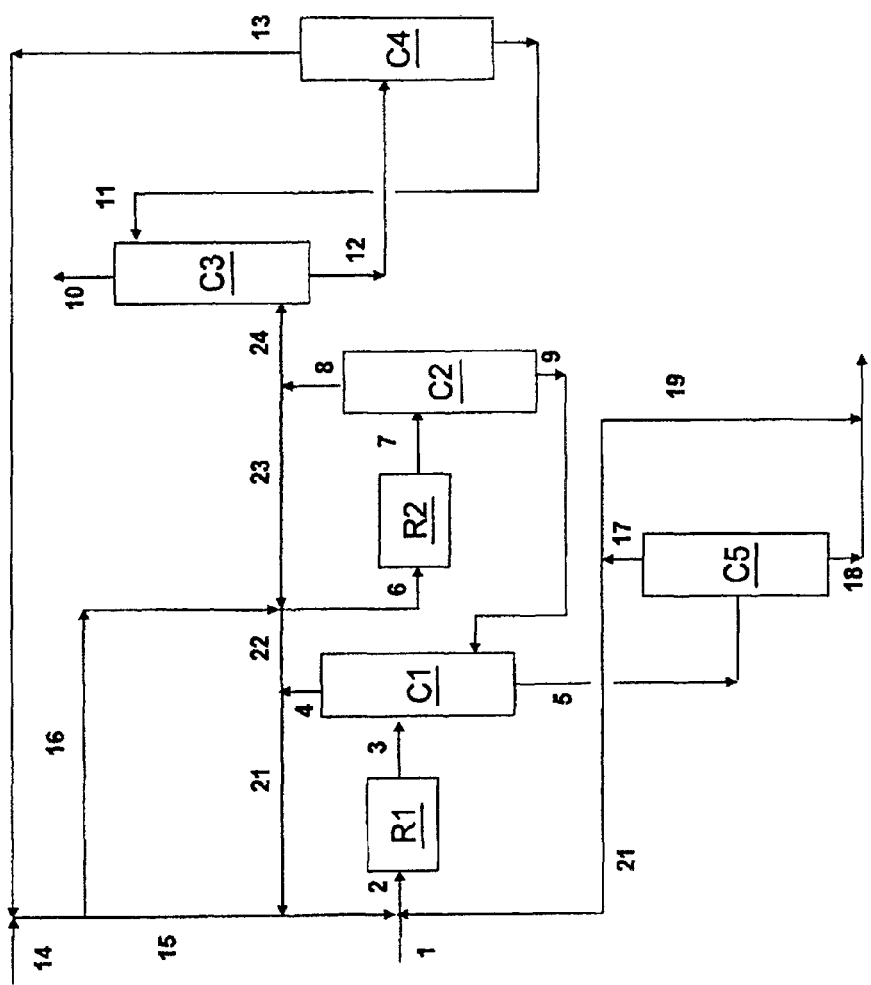
FIG. 3 shows a schematic diagram of an embodiment of the invention wherein partial recycling of streams of the separation columns is included.

This scheme can be further improved by means of a partial recycling, (21) and (23), of the streams at the head (4) and (8) of the two separation columns, C1 and C2, to the reaction steps, as shown in FIG. 3.

By operating in this way, it is possible:

to increase the total quantity of $C_4$ hydrocarbons in the reaction and in the separation column and consequently to also increase the quantity of alcohol which can be recovered at the heads of the two columns;

to increase the alcohol/isobutene molar ratio in the two reaction steps (reaction equilibrium shifted towards the product) as an increase in the alcohol content corresponds with a decrease in the concentration of isobutene as a result of the dilution;

to improve the total conversion of the isobutene in the first reaction step, as isobutene is still present in the stream 21, which thus passes various times through the catalytic beds.

Figure 4:
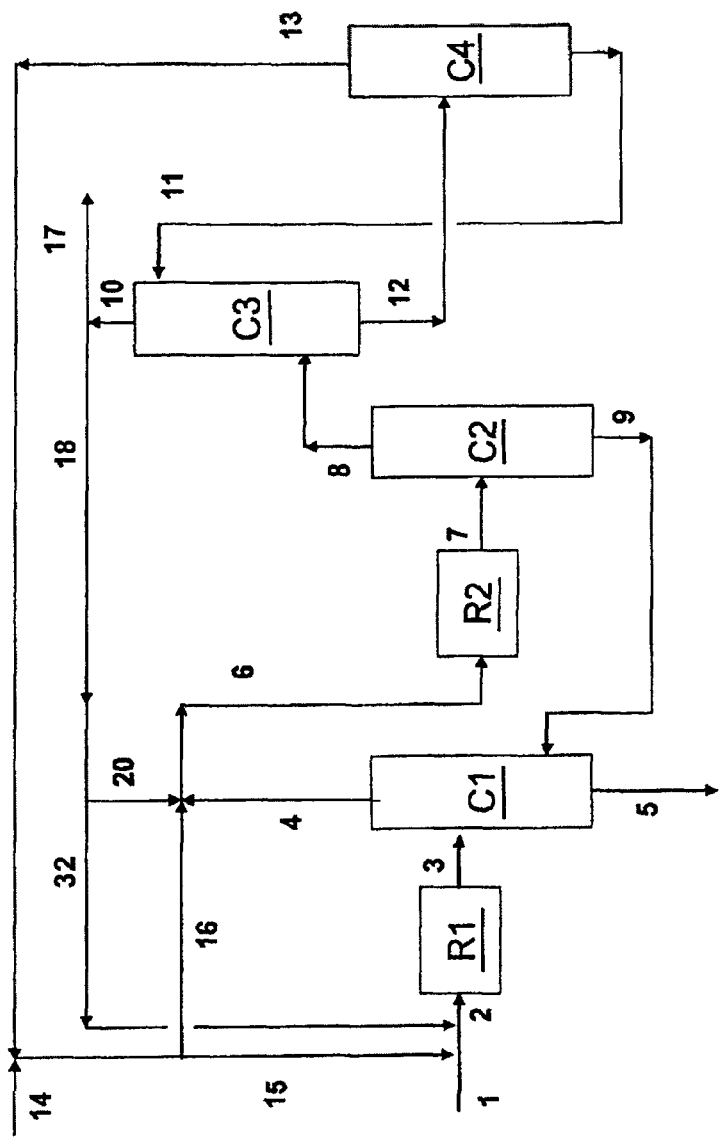
FIG. 4 shows a schematic diagram of an embodiment of the invention wherein a part of the hydrocarbon stream dilutes the reaction charges.

Alternatively, only a part of the hydrocarbon stream without isobutene can be used (before or after washing with water) to dilute, (32) and (20), both charges at the reaction steps, as shown in FIG. 4.

Figure 5:
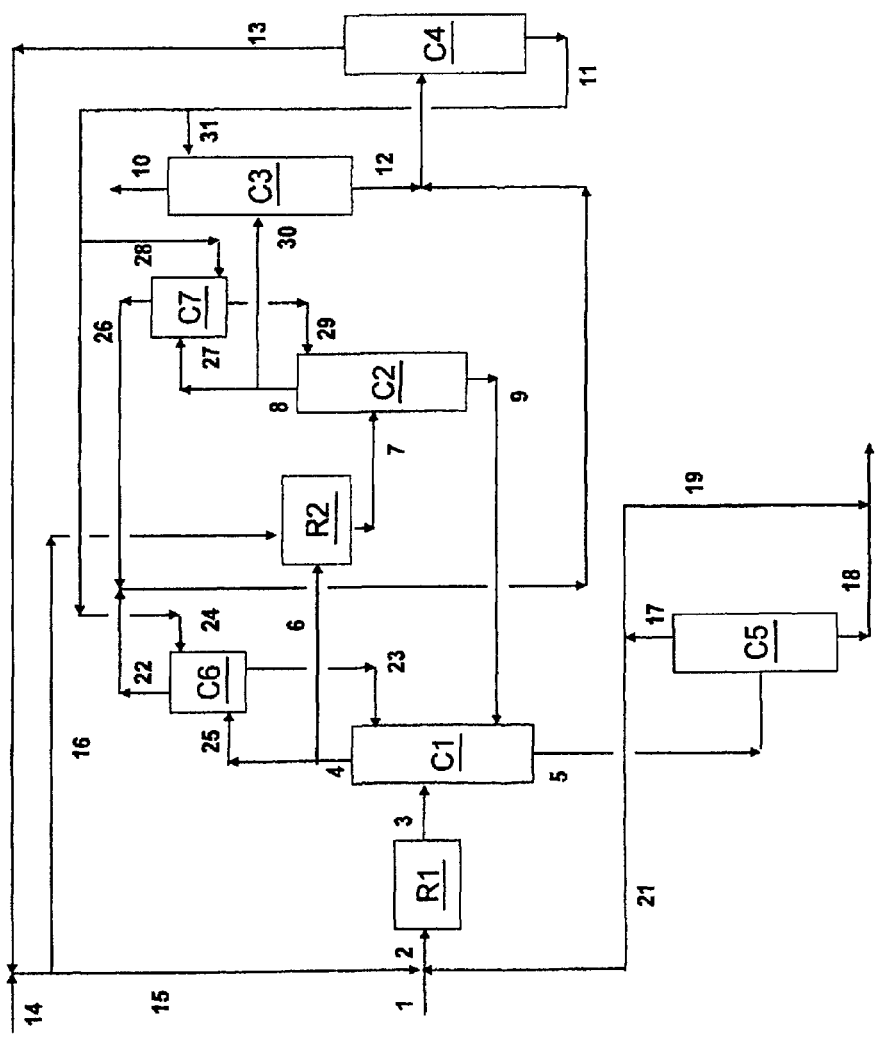
FIG. 5 shows a schematic diagram of an embodiment of the invention wherein two washing units are included.

A further improvement in the conversion can be obtained using the scheme shown in FIG. 5, which includes two washing sections C6 and C7. In this case a washing is carried out with water, in a single step, of the two streams (25 and (27), which represent the refluxes of the two separation columns, in order to remove most of the alcohol present in the stream. The use of a reflux (streams (23) and (29)) which is impoverished in oxygenated products, allows a higher amount of alcohol to be recovered at the head and therefore to use even higher alcohol/isobutene molar ratios in the two reaction steps. The hydro-alcoholic streams obtained after the two washings (22) and (26) are added to the stream (12) coming out of the washing column C3 and sent to column C4 for the recovery of the alcohol.

Figure 6:
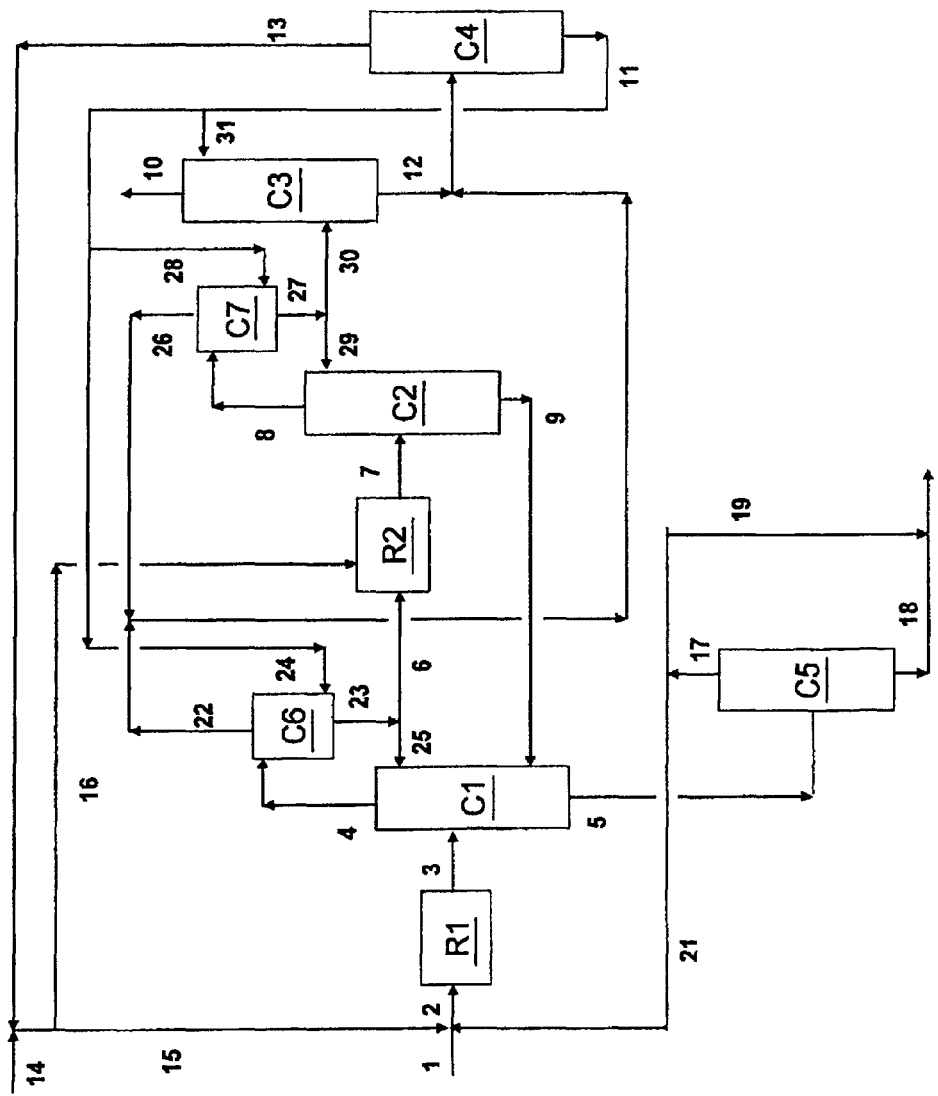
FIG. 6 shows a schematic diagram of an embodiment of the invention wherein vapors in the columns are condensed by direct addition of water.

FIG. 6 shows a slightly different scheme. In this case, vapors (4) and (8) which develop from the first plate of columns C1 and C2, are condensed by the direct addition of water (quenching), so as to obtain new streams (23) and (27) having a lower alcohol content, to be used for subsequent treatment, streams (6) and (30), or as reflux, streams (25) and (29) in columns C1 and C2.

Figure 7:
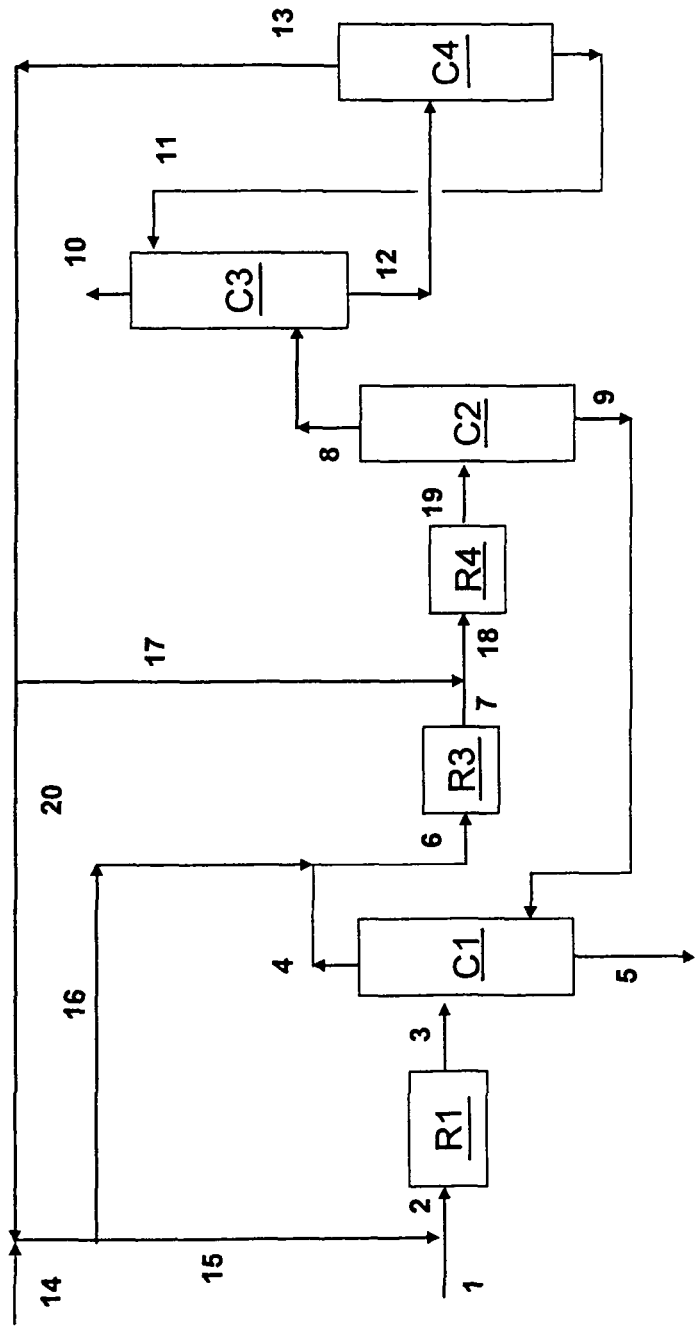
Figure 8:
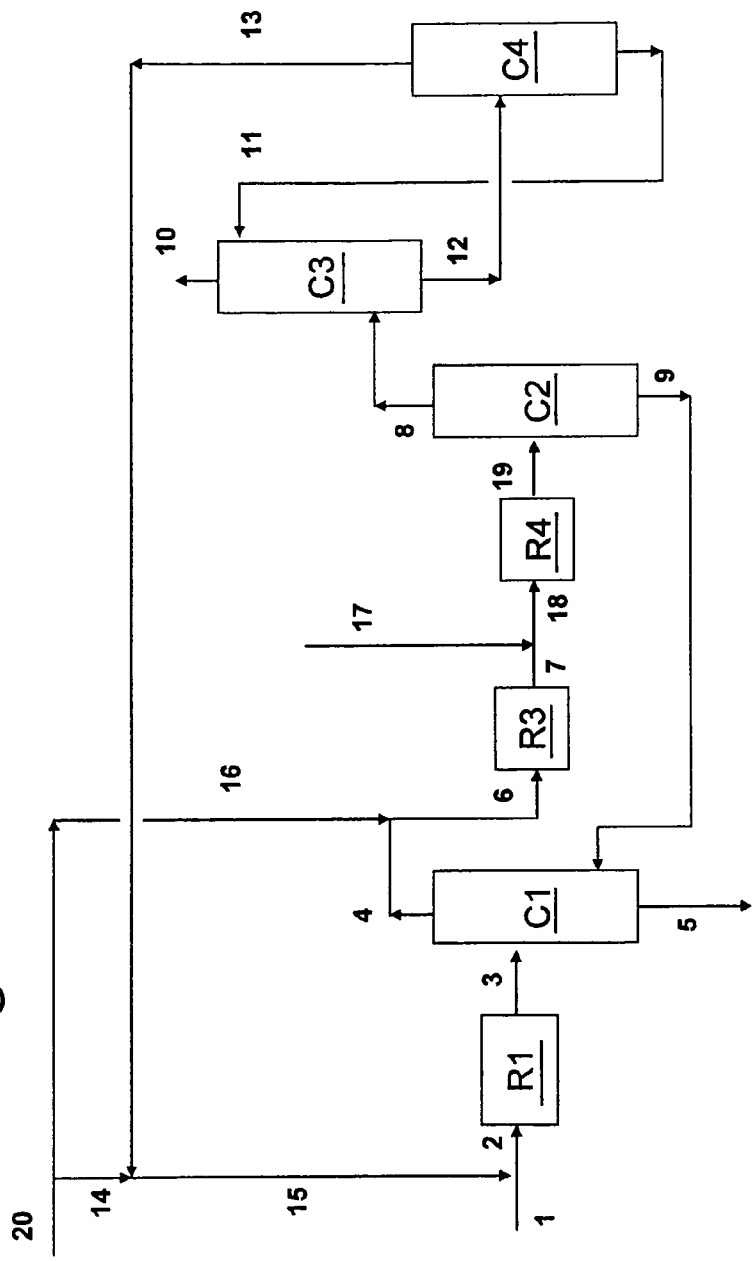

Finally, FIGS. 7 and 8 show a further plant configuration characterized in that it uses, in the second reaction step, at least two reactors in series R3 and R4 (possibly with an intermediate cooling) and adds at least one new reactive oxygenated compound (water and/or methanol). By operating in this way, the required isobutene conversion can be more easily reached, as, in addition to the synthesis of ETBE, isobutene is involved in a new reaction, far from the thermodynamic equilibrium.

In FIG. 7, an aliquot (17) of the azeotropic stream ethanol/water (13), obtained from the head of the alcohol recovery column C4, is fed to the reactor R4. In this way, in addition to the formation of ETBE, there is also the reaction with water of the residual isobutene to form TBA.

FIG. 8 shows the feeding of methanol (17) to the reactor R4, so as to form MTBE in addition to ETBE.

For both the schemes shown in FIGS. 7 and 8, the concentration of isobutene in the stream (18) is so low that the formation of the new compound (TBA and/or MTBE) in R4 does not significantly alter the purity of the ether produced (5).

The following example is provided to illustrate the present invention more clearly, it being understood that the invention is not limited to this example.

EXAMPLE 1

A Steam Cracking stream, having the composition shown in table IV, is etherified in the example.

TABLE IV composition of the hydrocarbon feed charge

|  | Kg/h | Weight % |
|---|---|---|
| Butadiene | 0.8 | 0.2 |
| Butanes | 27.5 | 9.8 |
| Isobutene | 100 | 30.0 |
| n-butenes | 199.3 | 59.8 |
| $C_5$ Hydrocarbons | 0.7 | 0.2 |

A very high conversion of isobutene can be obtained by applying the scheme shown in FIG. 2 (higher than 99%) together with a product within specification (2% by weight) as far as the ethanol content is concerned.

20% of the stream (17) containing the ether/alcohol azeotropic mixture, obtained in the separation column C5, must be recycled to the first reaction section, in order to obtain this result.

With this scheme, it is therefore possible to use effective ethanol/isobutene molar ratios within the two reaction steps (1.12 and 2.4 respectively) which are much higher than those normally used:

in the synthesis of ETBE, for example, wherein, with a traditional scheme such as that shown in U.S. Pat. No. 6,369,280, an ethanol/isobutene molar ratio of 0.97 is used, which allows conversions of isobutene of 95% to be obtained.

in the synthesis of MTBE, wherein however a methanol/isobutene molar ratio of 1.1 is sufficient for obtaining analogous conversions of isobutene, as shown in U.S. Pat. No. 4,503,265.

The invention claimed is:

1. A process for production of an alkyl ether, comprising:
a) feeding a $C_4$-$C_5$ hydrocarbon stream comprising isobutene and a stream comprising a linear alcohol, to a first reaction unit;
b) reacting at least a portion of the linear alcohol and isobutene in the presence of an acid catalyst in the first reaction unit to obtain a first reaction stream comprising a ter-butyl ether of the linear alcohol, $C_4$-$C_5$ hydrocarbons, the linear alcohol and unreacted isobutene;
c) removing the first reaction stream from the first reaction unit;
d) sending the first reaction stream to a first distillation unit and separating a light stream comprising an azeotropic mixture of the linear alcohol and the $C_4$-$C_5$ hydrocarbons, and isobutene from a heavy stream comprising the ter-butyl ether;
e) feeding the light stream and a stream comprising the linear alcohol to a second reaction unit;
f) further reacting the linear alcohol and unreacted isobutene to obtain a second reaction stream comprising the ter-butyl ether of the linear alcohol, the $C_4$-$C_5$ hydrocarbons, and the linear alcohol;
g) removing the second reaction stream from the second reaction unit;
h) sending the second reaction stream to a second distillation unit and separating a second light stream consisting of an azeotropic mixture of the linear alcohol and the $C_4$-$C_5$ hydrocarbons from a second heavy stream comprising the ter-butyl ether, part of the $C_4$-$C_5$ hydrocarbons and part of the linear alcohol;
i) sending the second heavy stream to the first distillation unit;
j) sending the second light stream to a linear alcohol recovery unit comprising a water washing column;
k) separating the linear alcohol as a water solution from the $C_4$-$C_5$ hydrocarbons;
l) separating the water from the linear alcohol to obtained recovered linear alcohol; and
m) recycling the recovered linear alcohol to at least one of the first and second reaction units;
wherein
part of the first light stream is condensed and recycled to the first reaction unit; and/or
part of the second light stream is condensed and recycled to at least one of the first and second reaction units, and
wherein the $C_4$-$C_5$ hydrocarbon stream from k) is partly recycled to at least one of the first and second reaction units, and
the linear alcohol is at least one of methanol and ethanol and correspondingly the ter-butyl ether is at least one of methyl ter-butyl-ether and ethyl ter-butyl ether.

2. The process according to claim 1, wherein the heavy stream containing the ter-butyl ether, separated in the first distillation unit, is sent to a third distillation unit wherein a stream is separated, consisting of substantially pure ter-butyl ether from a stream containing a ter-butyl ether/alcohol azeotropic mixture, which is divided into two streams, one of which is recycled to the first reaction unit, the second is mixed with the stream consisting of the substantially pure ter-butyl ether.

3. The process according to claim 1, wherein the light condensed stream leaving the first distillation unit is totally or partially sent to a water washing section.

4. The process according to claim 3, wherein two streams leave the water washing section, one containing water and linear alcohol is sent to the washing column, the other substantially containing $C_4$ hydrocarbons, is either totally or partially recycled, as reflux, to the first distillation unit.

5. The process according to claim 1, wherein the light condensed stream leaving the second distillation unit is totally or partially sent to a water washing column.

6. The process according to claim 5, wherein two streams leave the water washing column, a first stream containing water and linear alcohol sent to the distillation column of the water washing unit downstream of the second distillation area, and a second stream substantially containing $C_4$ hydrocarbons, either totally or partially recycled, as reflux, to the second distillation unit.

7. The process according to claim 1, wherein the light stream separated in the first distillation unit is in gaseous form.

8. The process according to claim 1, wherein the light stream separated in the second distillation unit is in gaseous form.

9. The process according to claim 7, wherein the light gaseous stream leaving the first distillation area is sent to a quenching section.

10. The process according to claim 9, wherein two streams leave the quenching section, downstream with respect to the first distillation unit, one containing water and linear alcohol, sent to the washing column the other containing mainly $C_4$ hydrocarbons, partially sent to the second reaction unit and partially recycled, as reflux, to the first distillation unit.

11. The process according to claim 8, wherein the light gaseous stream leaving the second distillation unit is sent to another quenching section.

12. The process according to claim 11, wherein two streams leave the quenching section, downstream with respect to the second distillation unit, one containing water and linear alcohol, sent to the washing column, the other containing mainly $C_4$ hydrocarbons, partially sent to the washing column, and partially recycled, as reflux, to the second distillation unit.

13. The process according to claim 1, wherein the second reaction unit comprises at least two reactors in series, between which an intermediate cooling system may optionally be present.

14. The process according to claim 13, wherein part of the stream leaving the head of the distillation column of the washing step with water is fed to the second or to the last of the reactors in series.

15. The process according to claim 13, wherein methanol is fed to the second or to the last of the reactors in series.

16. The process according to claim 1, wherein at least one of the first reaction unit and the second reaction unit comprises at least one of a tubular reactor and an adiabatic reactor.

17. The process according to claim 1, wherein the a temperature of the first reaction unit and the second reaction unit is from 30 to 100° C., at a pressure lower than 5 MPa and a feeding space velocity lower than 30 $h^{-1}$.

18. The process according to claim 17, wherein the feeding space velocities range from 1 to 15 $h^{-1}$.

19. The process according to claim 1 wherein $C_4$ and $C_5$ olefins present in the hydrocarbon stream react with the linear alcohol.

20. The process according to claim 1, wherein the isobutene content in the hydrocarbon stream is modified by dilution with $C_4$-$C_7$ streams.

21. The process according to claim 1, wherein the acid catalysts comprise sulfonated polymeric resins.

22. The process according to claim 13, wherein part of the stream leaving the head of the washing column is fed to the second or to the last of the reactors in series.

23. The process according to claim 1,
wherein the heavy stream containing the ter-butyl ether, separated in the first distillation unit, is sent to a third distillation unit wherein a stream is separated, consisting of substantially pure ter-butyl ether from a stream containing the ter-butyl ether/alcohol azeotropic mixture, which is divided into two streams, one of which is recycled to the first reaction unit, the second is mixed with the stream consisting of the substantially pure ether.

24. The process according to claim 1, wherein the alkyl ether is methyl ter-butyl-ether, the linear alcohol is methanol, and wherein pure methanol is recovered and recycled to at least one of the first and second reaction steps.

25. The process according to claim 1, wherein the alkyl ether is ethyl ter-butyl-ether, the linear alcohol is ethanol, and wherein an azeotropic mixture (93:7) of ethanol:water is recovered and recycled to at least one of the first and second reaction steps.

* * * * *